United States Patent
Salem et al.

(10) Patent No.: US 9,601,899 B2
(45) Date of Patent: Mar. 21, 2017

(54) ADJUSTABLE MID-INFRARED SUPER-CONTINUUM GENERATOR USING A TUNABLE FEMTOSECOND OSCILLATOR

(71) Applicant: THORLABS, INC., Newton, NJ (US)

(72) Inventors: Reza Salem, Columbia, MD (US); Peter Fendel, Sparta, NJ (US); Alex Cable, Newton, NJ (US)

(73) Assignee: Thorlabs, Inc., Newton, NJ (US)

( * ) Notice: Subject to any disclaimer, the term of this patent is extended or adjusted under 35 U.S.C. 154(b) by 0 days.

(21) Appl. No.: 14/589,509

(22) Filed: Jan. 5, 2015

(65) Prior Publication Data

US 2015/0288133 A1      Oct. 8, 2015

Related U.S. Application Data

(60) Provisional application No. 61/924,629, filed on Jan. 7, 2014.

(51) Int. Cl.
| | |
|---|---|
| *G01N 21/59* | (2006.01) |
| *H01S 3/11* | (2006.01) |
| *G01N 21/25* | (2006.01) |
| *G01N 21/35* | (2014.01) |
| *G01N 21/45* | (2006.01) |
| *G01N 21/47* | (2006.01) |

(Continued)

(52) U.S. Cl.
CPC .............. *H01S 3/11* (2013.01); *G01N 21/255* (2013.01); *G01N 21/35* (2013.01); *G01N 21/45* (2013.01); *G01N 21/47* (2013.01); *G01N 21/59* (2013.01); *G02B 21/0032* (2013.01); *G02B 21/0076* (2013.01); *G02B 21/361* (2013.01); *H01S 3/0092* (2013.01); *H01S 3/302* (2013.01); *G01N 2021/3595* (2013.01); *G02B 2207/114* (2013.01)

(58) Field of Classification Search
CPC .......... G02F 1/353; G02F 1/3532; H01S 3/10; H01S 3/30
See application file for complete search history.

(56) References Cited

U.S. PATENT DOCUMENTS

| | | | | |
|---|---|---|---|---|
| 8,787,410 B2 * | 7/2014 | Fermann | ........................... | 372/6 |
| 8,971,358 B2 * | 3/2015 | Fermann et al. | ................. | 372/6 |

(Continued)

FOREIGN PATENT DOCUMENTS

| | | |
|---|---|---|
| EP | 2 369 695 A2 | 9/2011 |
| WO | 2005094275 A2 | 10/2005 |

(Continued)

OTHER PUBLICATIONS

International Search Report with written opinion for international application PCT/US2015/010157, mailed Apr. 16, 2015.

(Continued)

*Primary Examiner* — Marcus Taningco
(74) *Attorney, Agent, or Firm* — Graham Curtin, P.A.

(57) ABSTRACT

A super-continuum system including: a fiber laser configured to output a pulse having a center wavelength; a first nonlinear waveguide configured to shift the wavelength of the pulse from the fiber laser; a first fiber amplifier of at least one stage configured to amplify the output from the first nonlinear waveguide; and a second nonlinear waveguide configured to spectrally broaden the output from the first fiber amplifier.

20 Claims, 3 Drawing Sheets

(51) Int. Cl.
   *G02B 21/00* (2006.01)
   *G02B 21/36* (2006.01)
   *H01S 3/00* (2006.01)
   *H01S 3/30* (2006.01)

(56) References Cited

U.S. PATENT DOCUMENTS

| | | | |
|---|---|---|---|
| 2004/0240037 A1* | 12/2004 | Harter | H01S 3/0057 359/333 |
| 2005/0238070 A1* | 10/2005 | Imeshev et al. | 372/21 |
| 2008/0013163 A1 | 1/2008 | Leonardo et al. | |
| 2009/0097512 A1* | 4/2009 | Clowes | G02B 21/16 372/21 |
| 2009/0204110 A1 | 8/2009 | Islam | |
| 2010/0054661 A1 | 3/2010 | Ramachandran | |
| 2011/0293273 A1 | 12/2011 | Futami | |
| 2013/0058366 A1* | 3/2013 | Leproux et al. | 372/25 |
| 2013/0188240 A1 | 7/2013 | Shaw et al. | |

FOREIGN PATENT DOCUMENTS

| | | |
|---|---|---|
| WO | 2011003190 A1 | 1/2011 |
| WO | 2011091316 A2 | 7/2011 |

OTHER PUBLICATIONS

International Search Report with written opinion mailed May 21, 2015 in correspondence with International Application No. PCT/US2015/010453.

USPTO Non-Final Office action mailed Sep. 28, 2016, for corresponding U.S. Appl. No. 14/591,489.

\* cited by examiner

ADJUSTABLE MID-INFRARED SUPER-CONTINUUM GENERATOR USING A TUNABLE FEMTOSECOND OSCILLATOR

CROSS-REFERENCE TO RELATED APPLICATIONS

This application claims the benefit of U.S. Provisional Application No. 61/924,629, filed on Jan. 7, 2014, the contents of which are incorporated herein by reference.

FIELD OF THE INVENTION

The present invention relates to the field of super-continuum systems, and more particularly to mid-infrared super-continuum generators and systems using a tunable femtosecond oscillator.

BACKGROUND

Broadband light sources in the mid-infrared (MIR) region (2 um to 10 um) are used, for example, in remote sensing, IR-counter measures, medical diagnostic and spectroscopy applications. While incoherent broadband MIR sources have been available for years and are used in spectroscopy, these sources have limited power spectral density and poor beam quality. Coherent broadband light sources based on nonlinear spectral broadening, widely known as super-continuum sources, have been studied in the visible and near-infrared (NIR) region of the optical spectrum. Recently, there has been interest in developing such super-continuum sources in the MIR region. Such super-continuum sources should have high power density, high beam quality and low noise (high coherence) in order to offer significant advantage over existing incoherent MIR sources.

Super-continuum sources in the MIR region have been realized and reported in current publications. Such systems can be placed in two general categories primarily in connection with the type of pump source that they use: (a) systems using a nanosecond or picosecond pulsed laser as the pump source, and (b) systems using a femtosecond pulsed laser as the pump source. It is generally understood that the systems falling into category (a) suffer from low shot-to-shot coherence. This lack of coherence is particularly evident in the noise characteristics of the generated spectrum and leads to spectral and temporal fluctuations from shot to shot. While these low-coherence systems are useful as powerful broadband light sources with high beam quality, their application in spectroscopy is largely limited due to the coherence problem. The systems falling into category (b) can be designed to have high coherence by carefully adjusting the properties of the femtosecond pump pulse as well as the nonlinear medium used for broadening the spectrum. Concerning the pump sources for this category, there are a number of laser systems used in prior art. It is desirable to have the pump wavelength in close proximity or within the wavelength region where the super-continuum is generated. Two types of femtosecond sources that have been used for MIR super-continuum generation include mode-locked fiber lasers based on Thulium or Holmium doped fibers, and optical parametric oscillators. The fiber lasers provide femtosecond pulses with high energies at a center wavelength close to 2000 nm and potentially out to 3500 nm. The fiber lasers used for this application in prior art had a fixed wavelength. In addition, the mode-locking mechanisms for these fiber lasers are still under research and development and the number of commercially available devices is limited. The optical parametric oscillators (OPO) provide femtosecond pulses with a tunable center wavelength. However, the OPOs are expensive systems that occupy a large space. Additionally, the average powers available from OPOs are limited when compared with fiber-based sources.

Therefore, there is a need for a low-cost and compact system to generate femtosecond pulses for mid-infrared super-continuum generation. Additionally, a method for adjusting the pulse parameters such as wavelength, peak power, energy, and polarization is required in order to optimize the spectral brightness, bandwidth, spectral flatness, and coherence of the super-continuum.

One concrete spectroscopy application would be to use the broadband sources in conjunction with a Fourier transform spectrometer and a sample processing unit. There has been recent development and commercialization of Fourier transform spectrometers in the MIR region. By developing the low-noise MIR broadband source, complete spectroscopy systems for the MIR can be provided, which would offer a significant advantage over existing spectroscopy systems.

SUMMARY

An embodiment of the invention provides a femtosecond fiber laser at the telecommunications band around 1550 nm and a tuneable wavelength shifting method that converts the pulse wavelength to the amplification band of Thulium or Holmium doped optical fibers (around 2000 nm). This approach offers two advantages: (a) the femtosecond fiber lasers at 1550 nm have been developed into reliable and stable systems in the recent years and are commercially available from several companies, and (b) the amount of wavelength shift in the system can be tuned, offering the capability to adjust and optimize the output super-continuum spectrum. The output average power can be scaled up using a fiber amplifier in the 1800 nm to 2100 nm wavelength range.

One embodiment of the present invention provides a super-continuum system including: a fiber laser configured to output a pulse having a center wavelength; a first nonlinear waveguide configured to shift the wavelength of the pulse from the fiber laser; a first fiber amplifier of at least one stage configured to amplify the output from the first nonlinear waveguide; and a second nonlinear waveguide configured to spectrally broaden the output from the first fiber amplifier.

Another embodiment of the present invention provides a method for operating super-continuum system that includes a fiber laser configured to output a pulse having a center wavelength; a first nonlinear waveguide configured to shift the wavelength of the pulse from the fiber laser; a fiber amplifier with at least one stage configured to amplify the output from the first nonlinear waveguide; and a second nonlinear waveguide configured to spectrally broaden the output from the first fiber amplifier, the method including: receiving a feedback from, the output of the first fiber amplifier or the output of the second nonlinear waveguide; and adjusting peak power, energy, wavelength or polarization of the pulse entering the second nonlinear waveguide.

DETAILED DESCRIPTION OF THE PREFERRED EMBODIMENTS

Figure 1:
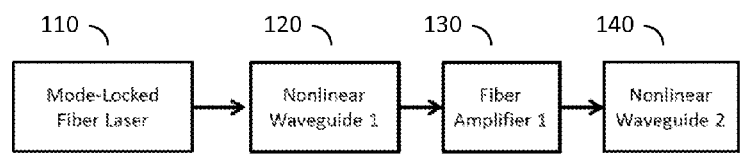
FIG. 1 is a block diagram of a super-continuum system in accordance with an embodiment of the invention.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

This disclosure describes the best mode or modes of practicing the invention as presently contemplated. This description is not intended to be understood in a limiting sense, but provides an example of the invention presented solely for illustrative purposes by reference to the accompanying drawings to advise one of ordinary skill in the art of the advantages and construction of the invention. In the various views of the drawings, like reference characters designate like or similar parts.

An embodiment of the invention is a system that comprises four key components, as shown in FIG. 1. The first component is a mode-locked fiber laser (MLFL) (110) supporting a transform-limited pulse width shorter than 1 ps and a center wavelength between 1500 nm and 1650 nm. The MLFL (110) is built based on a doped optical fiber as the gain medium and a mode-locking mechanism. The output from the fiber laser is coupled into Nonlinear Waveguide 1 (120), which shifts its wavelength to a wavelength longer than 1700 nm and shorter than 2800 nm by the process known as Raman salon self-frequency shifting. In one embodiment, Nonlinear Waveguide 1 (120) has an anomalous dispersion at the input pulse wavelength and a nonlinear coefficient larger than $1\ W^{-1}km^{-1}$. The third stage, Fiber Amplifier 1 (130), is a fiber amplifier operating in the wavelength region between 1700 nm and 2800 nm, for example, an amplifier system based on Thulium and/or Holmium doped fiber. In some embodiments, Fiber Amplifier 1 (130) is a dual or multi-stage amplifier. In some embodiments, Fiber Amplifier 1 (130) adds additional spectral bandwidth by nonlinear processes like self-phase modulation and/or compresses the pulses in addition to amplifying their energy. The amplifier output is coupled into Nonlinear Waveguide 2 (140), which is fabricated from a material that is transparent in the mid-infrared region. Said waveguide is designed to spectrally broaden the input pulse through non-linear processes such as hut not limited to Self-Phase Modulation, Modulation Instability and Raman scattering. It is advantageous if the Nonlinear Waveguide 2 (140) has a near zero dispersion point that is close to the center wavelength of the pulses exiting Fiber Amplifier 1 (130) and to then to fine tune the source to zero dispersion wavelength. Further is advantageous if the Nonlinear Waveguide 2 has anomalous dispersion at the center wavelength of the pulses exiting Fiber Amplifier 1 (130).

Figure 2:
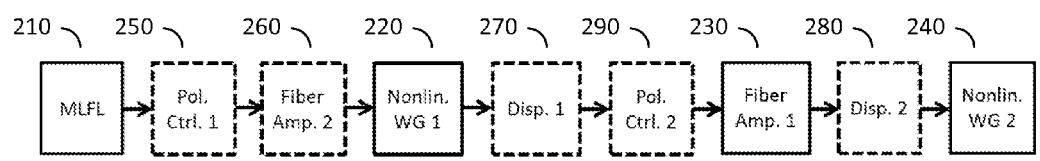
FIG. 2 is a block diagram of a super-continuum system in accordance with another embodiment of the invention.

In other embodiments of the invention, one or more of the following components can be added to the system to improve its performance, as shown in FIG. 2.

Fiber amplifier 2 amplifier 2 (260): A fiber amplifier can be included between the MLFL (210) and Nonlinear Waveguide 1 (220). The amplifier has a gain in the wavelength region from 1500 nm to 1650 nm, for example, an Er-doped fiber amplifier. The amplifier has three functions. First, it boosts the power from a low-power MLFL to the level needed for the Raman self-frequency shifting process. Second, it spectrally broadens and compresses the pulses from the mode-locked oscillator, which improves the efficiency of the frequency-shifting process, leading to a pulse energy increase or a pulse width decrease for the frequency-shifted pulses. Third, by adjusting the amplifier gain, it provides means for adjusting the amount of wavelength shift. The wavelength adjustment is used for the optimization of the output super-continuum parameters including its spectral brightness, bandwidth, spectral flatness, and coherence.

Polarization controller 1 (250): This device is a manual or an automated polarization controller inserted between the MLFL (210) and Nonlinear Waveguide 1 (220). The polarization controller is used as a second adjustment mechanism for controlling the amount of wavelength shift through the self-frequency shifting process. An automated controller can be used to dynamically tune the wavelength to a desired point in the spectrum for added stability.

Note that in one embodiment, polarization controller 1 (250) can be placed directly after the Mode-Locked Fiber Laser (210) or in between Fiber Amplifier 2 (260) and Nonlinear Waveguide 1 (220).

In some embodiments, the MLFL (210) and Fiber Amplifier 2 (260) are built using polarization maintaining fibers. In these cases, the wavelength shift is adjusted only using the gain of Fiber Amplifier 2 (260).

Dispersive Element 1 (270): This component is included after Nonlinear Waveguide 1 (220) in order to create a desired amount of chirp on the pulse entering Fiber Amplifier 2 (260). The component comprises a dispersive device, including but not limited to optical waveguides, chirped Bragg gratings, prism pairs, and diffraction grating pairs. In some embodiments, the dispersion value is designed to compress the output pulse from Fiber Amplifier 1 (230) to the shortest duration through the interplay between the dispersion and the nonlinearity in the amplifier. In other embodiments, Dispersive Element 1 is designed to increase the pulse duration in order to reduce the nonlinear effects in the amplifier. In such cases, the pulses are re-compressed using the Dispersive Element 2 (see below). The dispersion value is selected by monitoring the output super-continuum bandwidth, spectral flatness, and coherence, with the goal of optimizing the parameters.

In some embodiments it is advantageous to add a wavelength selecting element after Non-linear Waveguide 1 or within multiple stages of Fiber Amplifier 1 to adjust the output spectrum for Fiber Amplifier 1.

Polarization controller 2 (290): This component adjusts the polarization state of the pulses before entering Fiber Amplifier 1. By controlling this polarization state, the effective nonlinearity in Fiber Amplifier 1 can be adjusted, which is used to optimize the nonlinear pulse compression in Fiber Amplifier 1

Note that in one embodiment, polarization controller 2 (290) can be placed directly after Nonlinear Waveguide 1 (220) or in between Dispersive Element 1 (270) and Fiber Amplifier 1 (230).

In some embodiments, Fiber Amplifier 1 (230) is built using polarization maintaining fibers. In these cases, the nonlinearity in Fiber Amplifier 1 is adjusted using the gain of Fiber Amplifier 1 (230).

Dispersive Element 2 (280): This component is included before Nonlinear Waveguide 2 (240) as means to adjust the amount of chirp on the pulse entering the nonlinear waveguide. The component comprises a dispersive device, including but not limited to optical waveguides, chirped Bragg gratings, prism pairs, and diffraction grating pairs. The dispersion value is selected by monitoring the one or several of the following parameters: output super-continuum spectral brightness, bandwidth, spectral flatness, and coherence, with the goal of optimizing the parameters.

Figure 3:
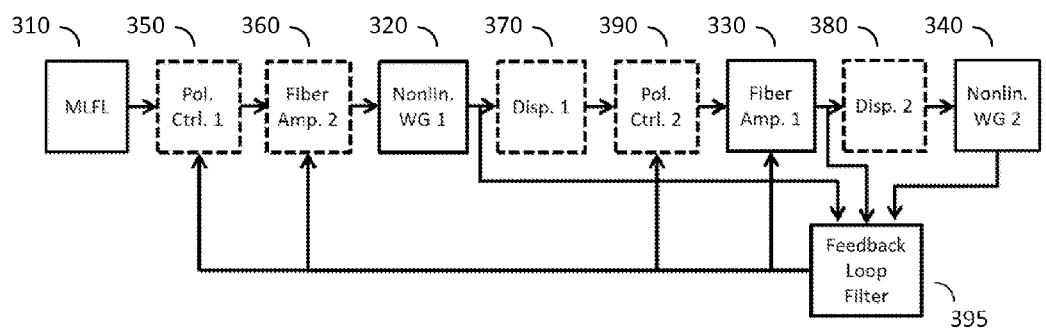
FIG. 3 is a block diagram of a super-continuum system in accordance with another embodiment of the invention.

In yet another embodiment another Polarization controller can be used between Fiber Amplifier 1 and Nonlinear Waveguide 2. The Polarization of the light entering Non-linear waveguide 2 will be adjusted to optimize one or several of the following parameters: output super-continuum spectral brightness, bandwidth, spectral flatness, and coherence, An embodiment of the invention provides a system and method for stabilizing and tuning the pump wavelength and pulse shape and consequently optimizing the parameters of the super-continuum by adjusting the gains of Fiber Amplifiers 1 or 2 (330 or 360), or the polarization controllers 1 or 2 (350 or 390), as shown in FIG. 3. As discussed above, in addition to the MLFL (310), Nonlinear Waveguide 1 (320), Fiber Amplifier 1 (330) and Nonlinear Waveguide 2 (340), one or more of the components: Polarization controller 1 (350), Fiber amplifier 2 amplifier 2 (360), Dispersive Element 1 (370), Polarization controller 2 (390) and Dispersive Element 2 (380) are optionally included. By receiving feedback via a Feedback loop filter (395) from the output super-continuum spectrum, the output from Nonlinear Waveguide 1 (320), or the output from Fiber Amplifier 1 (330), the variables (gain or polarization) are dynamically adjusted to stabilize the system to a desired state. The parameters are tuned in order to optimize the output spectral flatness, bandwidth, and coherence.

Second Raman Self-Frequency Shifting

Figure 4:
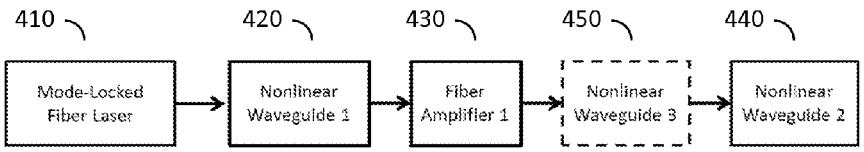
FIG. 4 is a block diagram of a super-continuum system in accordance with another embodiment of the invention.

In one embodiment, a second Raman self-frequency shifting process is added to the system comprising a MLFL (410), a Nonlinear Waveguide 1 (420), a Fiber Amplifier 1 (430) and a Nonlinear Waveguide 2 (440), to further push the pump pulse wavelength closer to the MIR region, as shown in FIG. 4. This Raman self-frequency shifting process occurs within Fiber Amplifier 1 (430), or in an intermediate section, Nonlinear Waveguide 3 (450), which is placed between Fiber Amplifier 1 (430) and Nonlinear Waveguide 2 (440). In this configuration, the pulse wavelength is shifted to a wavelength longer than 2100 nm but shorter than 3000 nm before it enters Nonlinear Waveguide 2 (440). This modification to the system provides two advantages:

(a) The output spectrum can be extended farther into the MIR region. It is well understood that the generated super-continuum can be shifted to longer wavelengths by shifting the pump pulse wavelength to longer wavelengths.

(b) Some nonlinear materials for MIR applications have zero-dispersion wavelengths that are longer than 2100 nm. The ability to pump the super-continuum source at wavelengths longer than 2100 nm allows the efficient generation of such continua using these nonlinear waveguides.

Nonlinear Waveguide 3 (450) has anomalous dispersion and is built of a material that transmits light in the wavelength range from 2100 nm to 3000 nm.

Note that in some embodiments, Fiber Amplifier 1 (430) also functions as a nonlinear waveguide, which creates Raman-shifted light. In such cases, Nonlinear Waveguide 3 (450) can be eliminated from the system.

Another embodiment of the invention is a system that comprises four key components, as shown in FIG. 1. The first component is a mode-locked fiber laser (MLFL) (110) supporting a transform-limited pulse width shorter than 1 ps and a center wavelength between 1900 nm and 2100 nm. The MLFL (110) is built based on a doped optical fiber as the gain medium and a mode-locking mechanism. The output from the fiber laser is coupled into Nonlinear Waveguide 1 (120), which shifts its wavelength to a wavelength longer than 2100 nm and shorter than 3500 nm by the process known as Raman soliton self-frequency shifting. In one embodiment, Nonlinear Waveguide 1 (120) has an anomalous dispersion at the input pulse wavelength and a nonlinear coefficient larger than $1\ W^{-1}km^{-1}$. The third stage, Fiber Amplifier 1 (130), is a fiber amplifier operating in the wavelength region between 2100 nm and 3500 nm, for example, an amplifier system based on Thulium and/or Holmium doped fiber. In some embodiments, Fiber Amplifier 1 (130) is a dual or multi-stage amplifier. In some embodiments, Fiber Amplifier 1 (130) adds additional spectral bandwidth by nonlinear processes like Self-phase modulation and/or compresses the pulses in addition to amplifying their energy. The amplifier output is coupled into Nonlinear Waveguide 2 (140), which is fabricated from a material that is transparent in the mid-infrared region. Said waveguide is designed to spectrally broaden the input pulse through non-linear processes such as but not limited to Self-Phase Modulation, Modulation Instability and Raman scattering. It is advantageous if the Nonlinear Waveguide 2 (140) has a near zero dispersion point that is close to the center wavelength of the pulses exiting Fiber Amplifier 1 (130) and to then to fine tune the source to zero dispersion wavelength. Further is advantageous if the Nonlinear Waveguide 2 has anomalous dispersion at the center wavelength of the pulses exiting Fiber Amplifier 1 (130).

In other embodiments of the invention, one or more of the following components can be added to the system to improve its performance, as shown in FIG. 2.

Fiber amplifier 2 amplifier 2 (260): A fiber amplifier can be included between the MLFL (210) and Nonlinear Waveguide 1 (220). The amplifier has a gain in the wavelength region from 1900 nm to 2100 nm, for example, an TM- or TM/HO-doped fiber amplifier. The amplifier has three functions. First, it boosts the power from a low-power MLFL to the level needed for the Raman self-frequency shifting process. Second, it compresses the pulses from the mode-locked oscillator, which improves the efficiency of the frequency-shifting process, leading to a pulse energy increase or a pulse width decrease for the frequency-shifted pulses. Third, by adjusting the amplifier gain, it provides means for adjusting the amount of wavelength shift. The wavelength adjustment is used for the optimization of the output super-continuum parameters including its spectral brightness, bandwidth, spectral flatness, and coherence.

Polarization controller 1 (250): This device is a manual or an automated polarization controller inserted between the MLFL (210) and Nonlinear Waveguide 1 (220). The polarization controller is used as a second adjustment mechanism for controlling the amount of wavelength shift through the self-frequency shifting process. An automated controller can be used to dynamically tune the wavelength to a desired point in the spectrum for added stability.

Note that in one embodiment, polarization controller 1 (250) can be placed directly after the Mode-Locked Fiber Laser (210) or in between Fiber Amplifier 2 (260) and Nonlinear Waveguide 1 (220).

In some embodiments, the MLFL (210) and Fiber Amplifier 2 (260) are built using polarization maintaining fibers. In these cases, the wavelength shift is adjusted only using the gain of Fiber Amplifier 2 (260).

Dispersive Element 1 (270): This component is included after Nonlinear Waveguide 1 (220) in order to create a desired amount of chirp on the pulse entering Fiber Amplifier 2 (260). The component comprises a dispersive device, including but not limited to optical waveguides, chirped Bragg gratings, prism pairs, and diffraction grating pairs. In some embodiments, the dispersion value is designed to compress the output pulse from Fiber Amplifier 1 (230) to the shortest duration through the interplay between the dispersion and the nonlinearity in the amplifier. In other embodiments, Dispersive Element 1 is designed to increase the pulse duration in order to reduce the nonlinear effects in the amplifier. In such cases, the pulses are re-compressed using the Dispersive Element 2 (see below). The dispersion value is selected by monitoring the output super-continuum bandwidth, spectral flatness, and coherence, with the goal of optimizing the parameters.

Polarization controller 2 (290): This component adjusts the polarization state of the pulses before entering Fiber Amplifier 1. By controlling this polarization state, the effective nonlinearity in Fiber Amplifier 1 can be adjusted, which is used to optimize the nonlinear pulse compression in Fiber Amplifier 1.

In some embodiments, Fiber Amplifier 1 (230) is built using polarization maintaining fibers. In these cases, the nonlinearity in Fiber Amplifier 1 is adjusted using the gain of Fiber Amplifier 1 (230).

Note that in one embodiment, polarization controller 2 (290) can be placed directly after Nonlinear Waveguide 1 (220) or in between Dispersive Element 1 (270) and Fiber Amplifier 1 (230).

Dispersive Element 2 (280): This component is included before Nonlinear Waveguide 2 (240) as means to adjust the amount of chirp on the pulse entering the nonlinear waveguide. The component comprises a dispersive device, including but not limited to optical waveguides, chirped Bragg gratings, prism pairs, and diffraction grating pairs. The dispersion value is selected by monitoring the one or several of the following parameters: output super-continuum spectral brightness, bandwidth, spectral flatness, and coherence, with the goal of optimizing the parameters.

An embodiment of the invention provides a system and method for stabilizing and tuning the pump wavelength and pulse shape and consequently optimizing the parameters of the super-continuum by adjusting the gains of Fiber Amplifiers 1 or 2 (330 or 360), or the polarization controllers 1 or 2 (350 or 390), as shown in FIG. 3. As discussed above, in addition to the MLFL (310), Nonlinear Waveguide 1 (320), Fiber Amplifier 1 (330) and Nonlinear Waveguide 2 (340), one or more of the components: Polarization controller 1 (350), Fiber amplifier 2 amplifier 2 (360), Dispersive Element 1 (370), Polarization controller 2 (390) and Dispersive Element 2 (380) are optionally included. By receiving feedback via a Feedback loop filter (395) from the output super-continuum spectrum, the output from Nonlinear Waveguide 1 (320), or the output from Fiber Amplifier 1 (330), the variables (gain or polarization) are dynamically adjusted to stabilize the system to a desired state. The parameters are tuned in order to optimize the output spectral flatness, bandwidth, and coherence.

SC Generation With Two Seed Wavelengths

Figure 5:
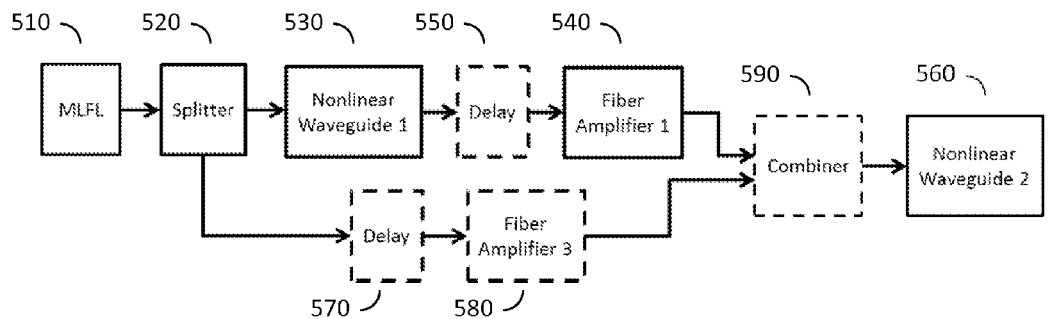
FIG. 5 is a block diagram of a super-continuum system in accordance with another embodiment of the invention.

In some cases, it can be beneficial to extend or smoothen the SC to seed the Nonlinear Waveguide 2 (560) discussed above, with two different wavelengths via a splitter (520), as shown in FIG. 5. One wavelength could be produced by the MLFL (510) directly while the second seed wavelength would be produced by non-linear waveguide 1 (530) and amplified by Fiber Amplifier 1 (540).

In some embodiments, Fiber Amplifier 3 (580) is used for boosting the power that is split from the MLFL.

In some embodiments, a combiner (590) is used to combine the light in the two paths before entering Nonlinear Waveguide 2.

In some embodiments, variable delay element (550) adjusts the delay of the pulses in the first path or variable delay element (570) adjusts the delay of the pulses in the second path.

Note that in one embodiment, this approach can be combined with the embodiment described above in the Second Raman Self-Frequency Shifting section. In this case, one wavelength is produced by the MLFL while the second seed wavelength would be produced by Nonlinear Waveguide 3.

Femtosecond MIR Pulse Generation by Wave Mixing

Figure 6:
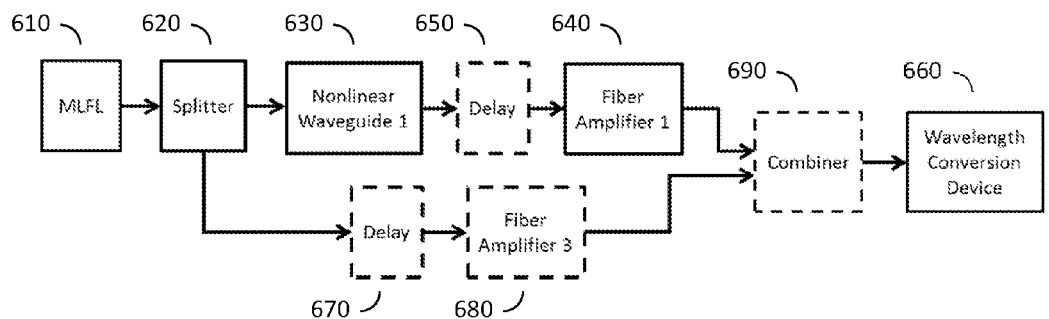
FIG. 6 is a block diagram of a super-continuum system accordance with another embodiment of the invention.

In one embodiment, as shown in FIG. 6, part of the optical power from the MLFL (610) is split by a splitter (620) placed before the Nonlinear Waveguide 1 (630), and is mixed with the output from Fiber Amplifier 1 (640) in a wavelength conversion device (660). An adjustable delay line (650) is placed on the beam path aligns the pulses in the time domain. In some embodiments, a fiber amplifier 3 (680) is used tier increasing the power that is split from the mode-locked fiber laser (610) output. In this case an additional adjustable delay line (670) may be placed before the Fiber Amplifier 3 (680). In some embodiments, a combiner (690) is used for combining the light from the two paths before entering the wavelength conversion device.

There are two categories of devices used for wavelength conversion:

(a) Difference frequency generation devices

The wavelength conversion device is built from a material with second-order optical nonlinearity. In this case, output pulses have a center frequency that is the difference between the center frequencies of the outputs from the MLFL and Fiber Amplifier 1. The generated pulses have a center wavelength between 3500 nm and 11000 nm.

(b) Four-wave mixing devices

The wavelength conversion device is based on nonlinear waveguides with a zero dispersion point close to the wavelength of the pulses exiting Fiber Amplifier 1. In this case, output pulses have a center frequency that is calculated by subtracting the center frequency of the mode-locked laser output pulses from twice the center frequency of Fiber Amplifier 1 output pulses. The generated pulses have a center wavelength between 2300 nm and 11000 nm.

Note that the frequency mixing concept explained here can be combined with the embodiment described above in the Second Raman Self-Frequency Shifting section. The mixing can occur between the outputs from Nonlinear Waveguide 3 and Fiber Amplifier 1, or the outputs from Nonlinear Waveguide 3 and Fiber Amplifier 3.

Figure 7:
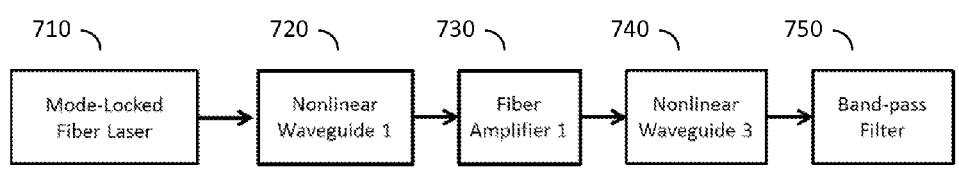
FIG. 7 is a block diagram of a super-continuum system in accordance with another embodiment of the invention.

An embodiment is related to the configuration described in the Second Raman Self-Frequency Shifting section, as shown in FIG. 7. As discussed above, the output from MLFL (710) is coupled to Nonlinear Waveguide 1 (720), and amplified by Fiber Amplifier 1 (730). By sending the pulses from Nonlinear Waveguide 3 (740) into a band-pass filter (750), only the Raman-shifted component is selected, which contains a femtosecond pulse train at a center wavelength longer than 2100 nm. The system produces pulses between 2100 nm and 3000 nm.

Note that, as described in the Second Raman Self-Frequency Shifting section, in some embodiments, Fiber Amplifier 1 also functions as a nonlinear waveguide, which creates Raman-shifted light. In such cases, Nonlinear Waveguide 3 can be eliminated from the system.

Mid-IR Spectroscopy System

Figure 8:
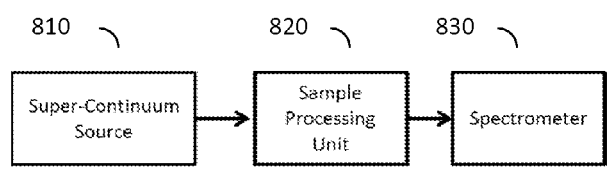
FIG. 8 is a block diagram of a super-continuum system in accordance with another embodiment of the invention.

In one embodiment, a complete spectroscopy system can be built using the SC source as described above. As shown in FIG. 8, the system includes three main sub-systems: the SC source (810), a sample processing unit (820), and a spectrometer or interferometer (830) to analyze the light transmitted, reflected or scattered from the sample. In some embodiments, the spectrometer is a Fourier-transform infrared spectrometer (FTIR). The sample processing unit (820) is any mount or enclosure that would allow the light from the SC source (810) to pass through, reflect or scatter off a sample. The sample could be any material in liquid, gas or solid form. The method described for tuning the SC spectral properties can be used to maximize the spectral coverage of the system by performing multiple spectral scans while tuning the SC output spectrum.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. A super-continuum system comprising:
   a mode-locked fiber laser with an optical bandwidth corresponding to a transform limited pulse duration of less than 1 ps and a pulse repetition rate of more than 1 MHz configured to output a pulse having a center wavelength;
   a first nonlinear waveguide configured to shift the wavelength of the pulse from the mode-locked fiber laser;
   a first fiber amplifier of at least one stage configured to amplify the output from the first nonlinear waveguide and further configured to output femtosecond pulses by using the interplay between the dispersion and nonlinearity in the first fiber amplifier; and
   a second nonlinear waveguide with a zero-dispersion point that is close to the center wavelength of the pulses exiting the first fiber amplifier configured to spectrally broaden the output from the first fiber amplifier by self-phase modulation.

2. The system of claim 1, wherein the first nonlinear waveguide shifts the output wavelength from the mode-locked fiber laser to a wavelength longer than 1700 nm and shorter than 2800 nm.

3. The system of claim 2, wherein the first fiber amplifier operates in the wavelength region between 1700 nm and 2800 nm.

4. The system of claim 1, wherein the second nonlinear waveguide is fabricated from a material with some transparency in the mid-infrared region.

5. The system, of claim 1, wherein the second nonlinear waveguide has anomalous dispersion at the center wavelength of the pulses exiting the first fiber amplifier.

6. The system of claim 1, further comprising a second fiber amplifier configured to boost the power from the mode-locked fiber laser and to control the amount of wavelength shift.

7. The system of claim 1, further comprising a first polarization controller for controlling an amount of wavelength shift through a Raman soliton self-frequency shifting process.

8. The system of claim 1, further comprising a first dispersive element configured to create a desired amount of chirp on the pulse entering the second fiber amplifier.

9. The system of claim 1, further comprising a second polarization controller configured to adjust the polarization state of the pulses entering the first fiber amplifier.

10. The system of claim 1, further comprising a second dispersive element configured to adjust the amount of chirp on the pulse entering the second nonlinear waveguide.

11. The system of claim 1, further comprising a third polarization controller to adjust the polarization state of the pulses entering the second nonlinear waveguide.

12. The system of claim 1, further comprising a third nonlinear waveguide placed between the first fiber amplifier and the second nonlinear waveguide to shift the wavelength of the output from the first fiber amplifier.

13. The system of claim 1, further comprising a splitter after the second fiber amplifier for splitting the output of the mode-locked fiber laser into a first path and a second path, the output on the first path is coupled to the first nonlinear waveguide and the light from the first fiber amplifier is combined with the output of the second path and coupled to the second nonlinear waveguide, in order to seed the second nonlinear waveguide with two different wavelengths.

14. The system of claim 1, further comprising a splitter after the mode-locked fiber laser for splitting the output of the mode-locked fiber laser into a first path and a second path, the output on the first path is coupled to the first nonlinear waveguide and the light from the first fiber amplifier is combined with the output of the second path and coupled to the second nonlinear waveguide, in order to seed the second nonlinear waveguide with two different wavelengths.

15. The system of claim 14, further comprising a variable delay line on the first path or on the second path.

16. The system of claim 14, further comprising a third fiber amplifier on the second path.

17. The system of claim 1, further comprising a band-pass filter configured to select a spectral band in the output pulse.

18. A method for operating super-continuum system that comprises a mode-locked fiber laser with an optical bandwidth corresponding to a transform limited pulse duration of less than 1 ps and a pulse repetition rate of more than 1 MHz configured to output a pulse having a center wavelength; a first nonlinear waveguide configured to shift the wavelength of the pulse from the mode-locked fiber laser; a first fiber amplifier with at least one stage configured to amplify the output from the first nonlinear waveguide and further configured to output femtosecond pulses by using the interplay between the dispersion and nonlinearity in the first fiber amplifier; and a second nonlinear waveguide with a zero-dispersion point that is close to the center wavelength of the pulses exiting the first fiber amplifier configured to spectrally broaden the output from the first fiber amplifier by self-phase modulation, the method comprising:
receiving a feedback from, via a feedback loop filter, the output of the first fiber amplifier or the output of the second nonlinear waveguide; and
dynamically adjusting peak power, energy, wavelength or polarization of the pulse entering the second nonlinear waveguide based on the feedback.

19. A spectroscopy system, comprising:
a mode-locked fiber laser with an optical bandwidth corresponding to a transform limited pulse duration of less than 1 ps and a pulse repetition rate of more than 1 MHz configured to output a pulse having a center wavelength;
a first nonlinear waveguide configured to shift the wavelength of the pulse from the mode-locked fiber laser;
a first fiber amplifier of at least one stage configured to amplify the output from the first nonlinear waveguide and further configured to output femtosecond pulses by using the interplay between the dispersion and nonlinearity in the first fiber amplifier;
a second nonlinear waveguide with a zero-dispersion point that is close to the center wavelength of the pulses exiting the first fiber amplifier configured to spectrally broaden the output from the first fiber amplifier by self-phase modulation;
a sample processing unit configured to direct the light output from the super-continuum system to pass through or reflect off a sample; and
a spectrometer or interferometer configured to analyze the light that passes through, reflects off or is scattered by the sample.

20. A method for increasing the spectral coverage of a spectroscopy system that comprises: a mode-locked fiber laser with an optical bandwidth corresponding to a transform limited pulse duration of less than 1 ps and a pulse repetition rate of more than 1 MHz configured to output a pulse having a center wavelength; a first nonlinear waveguide configured to shift the wavelength of the pulse from the mode-locked fiber laser; a first fiber amplifier of at least one stage configured to amplify the output from the first nonlinear waveguide and further configured to output femtosecond pulses by using the interplay between the dispersion and nonlinearity in the first fiber amplifier; a second nonlinear waveguide with a zero-dispersion point that is close to the center wavelength of the pulses exiting the first fiber amplifier configured to spectrally broaden the output from the first fiber amplifier by self-phase modulation; a sample processing unit configured to direct the light output from the super-continuum system to pass through or reflect off a sample; and a spectrometer or interferometer configured to analyze the light that passes through, reflects off or is scattered by the sample, the method comprising:
performing multiple spectral measurements while adjusting one or more parameters of the super-continuum spectrum.

* * * * *